(12) United States Patent
Webber et al.

(10) Patent No.: US 6,834,784 B1
(45) Date of Patent: Dec. 28, 2004

(54) GLOVE RETAINING DEVICE

(76) Inventors: Paul Hackett Webber, P.O. Box 114, Rio Nido, CA (US) 95471; Slavko Alex Limonczenko, P.O. Box 1135, Guerneville, CA (US) 95446

( * ) Notice: Subject to any disclaimer, the term of this patent is extended or adjusted under 35 U.S.C. 154(b) by 0 days.

(21) Appl. No.: 10/280,229

(22) Filed: Oct. 25, 2002

(51) Int. Cl.[7] .............................................. A47G 25/80
(52) U.S. Cl. ...................................................... 223/111
(58) Field of Search ................................ 223/111, 112, 223/119, 120; 2/318, 317

(56) References Cited

U.S. PATENT DOCUMENTS

| | | | | |
|---|---|---|---|---|
| 3,695,493 A | * | 10/1972 | Karr | 223/111 |
| 4,915,272 A | * | 4/1990 | Vlock | 223/111 |
| 5,058,785 A | * | 10/1991 | Rich et al. | 223/111 |
| 6,021,935 A | * | 2/2000 | Yonezawa | 223/111 |
| 6,053,380 A | * | 4/2000 | Sherrod | 223/111 |
| 6,279,792 B1 | * | 8/2001 | Neal | 223/111 |
| 6,554,168 B2 | * | 4/2003 | Stobart | 223/111 |

* cited by examiner

Primary Examiner—John J. Calvert
Assistant Examiner—James Smith
(74) Attorney, Agent, or Firm—Risto A. Rinne, Jr.

(57) ABSTRACT

An apparatus for removing a glove from a hand and retaining it in position includes a housing and a pair of self-facing arcuate members disposed on the inside thereof of opposite side walls of the housing. A plurality of downward facing bristles are attached to a lower portion of each of the arcuate members that are disposed in close proximity to each other. When a gloved hand is inserted into the device in a downward directions the arcuate members flex in toward the side walls to accommodate the gloved hand and the bristles allow for easy downward passage. When the hand is then withdrawn in an upward direction, the arcuate members force the bristles to bear into the glove preventing the glove from being extracted in an upward direction. Accordingly, the glove is retained in the device as the hand is pulled upward out from the device. Foam spacers provide additional force to urge the arcuate members toward the glove.

11 Claims, 2 Drawing Sheets

GLOVE RETAINING DEVICE

BACKGROUND OF THE INVENTION

1. Field of the Invention

The present invention, in general relates to tools and, more particularly, to devices that remove and secure gloves and mittens.

There are numerous situations when a person who is wearing gloves (or mittens) has need to remove one or both of them for a period of time. Often, working with a glove or mitten does not afford a sufficient amount of dexterity and the use of the fingers and hands, unencumbered by the glove or mitten, is needed. Sometimes only one of the gloves or mittens must be removed. At other times both of them must be removed.

Usually, the glove or mitten is removed and placed on a table, in a coat pocket, or on the ground. Later, when the task is finished, the user may forget to reclaim the glove or mitten or it may become lost among other items. As such, the user finds that he has lost one or both of his gloves. Missing one of a pair of gloves renders the other useless, and so the loss is total.

Even when the location of the glove or mitten is known, the need to have it readily accessible for wear and quickly removable when needed is desirable. For example, a house painter may be applying caulking from a caulking gun. He may frequently need to remove a glove from one hand when he wishes to use a finger to smooth the caulk bead, for example, around a window pane.

The user, in this instance, does not want to have to store the glove in a coat pocket each time it is not needed and then remove it every time it is required for use. Neither does he want to leave it behind and have to retrace his steps to reclaim it.

Furthermore, there are many instances when the user cannot even use one of his hands to assist in removing the glove from the remaining hand. If, for example, the house painter is using one hand to hold himself secure to a ladder, he takes a risk if he releases his secure hold of the ladder to free up both hands, one hand from which the glove is to be removed and the other hand to aid in removing the glove.

A device that permits a user to remove a glove from his hand without using the other hand is needed. The glove that is being removed may be soiled, contaminated, covered with wet paint, or have a toxic substance on it. The user may wish to avoid any physical contact with the glove that is being removed. A surgeon, for example, may need to change protective gloves without compromising the sterility of his hands. Therefore, he cannot remove one glove (using the other gloved-hand) and then remove the remaining glove with his ungloved hand.

Similarly, a worker involved with toxic substance cleanup may not wish to touch a contaminated glove in order to remove it from his hand. Furthermore, the contaminated glove must be retained for later disposal. It cannot simply be tossed in the trash for disposal at a land fill. Therefore, the glove must be retained by the worker for a later, safe disposal.

Furthermore, there are vast range in the sizes of gloves and mittens. The material they are formed from, their intended use, and the size of the hand greatly affect the size, and therefore the thickness, of the glove or mitten. For example, large welding gloves intended to fit a large man's hand will tend to be heavy, large, and thick whereas a gardening glove designed for use by a woman having small hands will tend to be much lighter and thinner. Accordingly, it is desirable to be able to readily remove and retain gloves or mittens of vastly different sizes.

Accordingly, there exists today a need for a glove retaining device that is adapted to secure a glove or mitten and which permits removal of the glove or mitten without using the remaining hand.

Clearly, such an apparatus would be a useful and desirable device.

2. Description of Prior Art

Gloves and mittens are, in general, known. Devices to secure articles of clothing are known, for example, coat hangers. The only known prior art to secure a glove or a mitten is a simulated hand, such as the hand of a mannequin, commonly found at department and clothing stores. While the structural arrangements of the above described devices, at first appearance, may have some distant similarities with the present invention, they differ in profound and material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a glove retaining device that is adapted to retain a glove or a mitten therein.

It is also an important object of the invention to provide a glove retaining device that is adapted to retain a plurality of gloves or mittens therein.

Another object of the invention is to provide a glove retaining device that is adapted to receive a hand that has a glove or mitten covering it.

Still another object of the invention is to provide a glove retaining device that is adapted to receive a hand that has a glove or mitten covering it and to retain the glove or mitten when the hand is removed from the device.

Still yet another object of the invention is to provide a glove retaining device that is adapted to receive a hand that has a glove or mitten covering it and to remove the glove or mitten from the hand when the hand is removed from the device.

Yet another important object of the invention is to provide a glove retaining device that is adapted to attach to a belt or clip onto a pair of trousers.

Still yet another important object of the invention is to provide a glove retaining device that allows easy removal of a glove or a mitten from the device.

Still yet one other important object of the invention is to provide a glove retaining device that is adapted to retain gloves or mittens of different size.

Briefly, a glove retaining device that is constructed in accordance with the principles of the present invention has a housing that includes a pair of parallel planar side walls that are disposed a predetermined distance apart from each other. A pair of arcuate members are attached to each of the side walls on the inside of the device. The arcuate members include a lower planar portion that is disposed in parallel planar alignment with respect to the side walls and is disposed a predetermined distance therefrom. A plurality of downward facing bristles are attached to each of the lower planar portions. The bristles of one arcuate member face the bristles of the remaining arcuate member. A foam spacer is disposed intermediate each arcuate member and each side wall. To use the device, a gloved hand is pushed down into the device, which has an open top and bottom. The bristles allow easy passage of the gloved hand into the device and the arcuate members compress the foam spacers to accommodate the gloved hand. Once the hand is sufficiently far in the device, its downward progress is stopped and the hand is withdrawn from the device in an opposite, upward direction. The foam spacers and the arcuate members urge the bristles into the glove sufficient to retain the glove as the hand is pulled upward, thereby removing the glove from the hand and retaining it in position in the device.

DETAILED DESCRIPTION OF THE INVENTION

Figure 1:
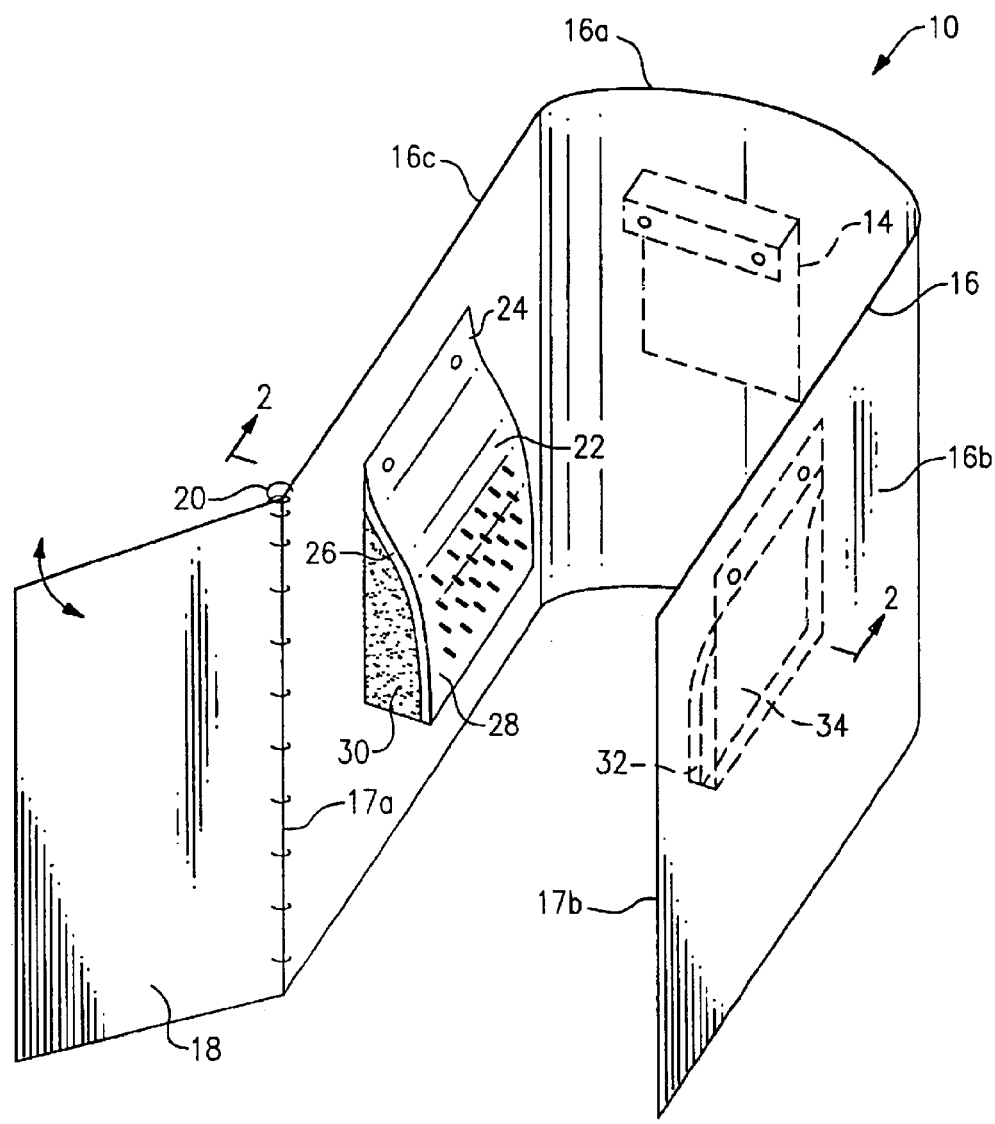
FIG. 1 is a view in perspective of a glove retaining device.
Figure 2:
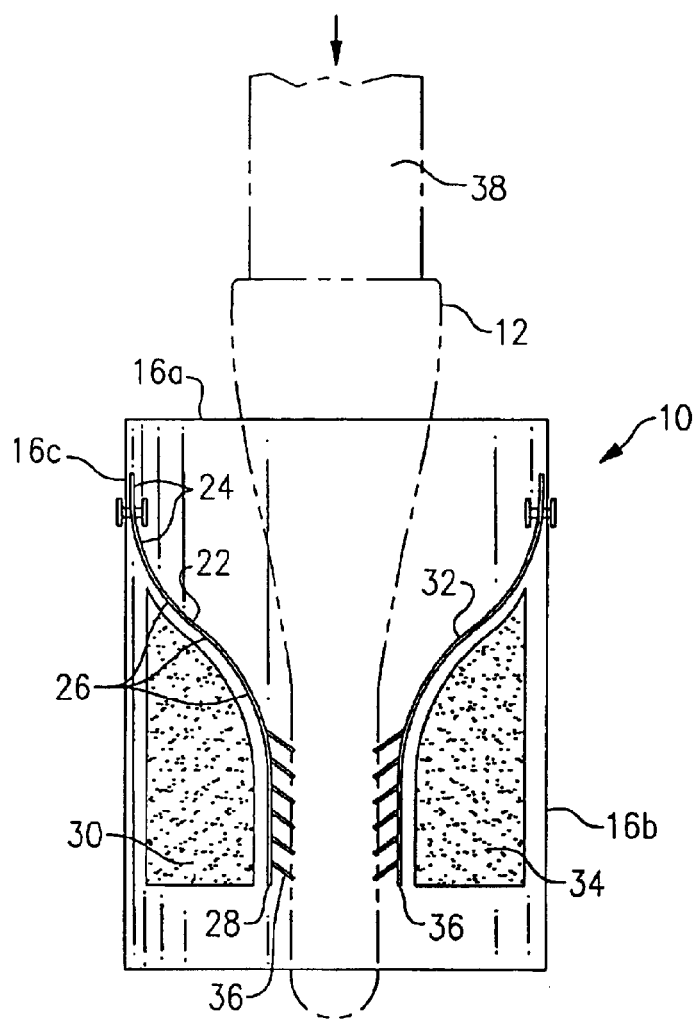
FIG. 2 is a cross sectional view taken on the line 2—2 in FIG. 1 with a glove inserted therein, the glove shown in dashed lines.

Referring to all three figures and especially now to both FIG. 1 and FIG. 2 is shown, a glove retaining device, identified in general by the reference numeral 10.

The device 10 is adapted to secure a glove 12 therein. While use of the glove 12 is described in detail, it is understood that any type of a mitten (not shown) may be substituted for the glove 12 and used in like manner.

Also, while the device 10 is described for use with the one glove 12 it is also possible to use the device 10 to secure a pair of the gloves 12 (or mittens), as desired. It is also possible, and in several ways preferable, to use a second device 10, one on either side of a torso, when securing the pair is required, with each device 10 being used to secure one of the gloves 10. This is described in greater detail hereinafter.

A belt clip 14 (shown in FIG. 1 in dashed lines) is attached to a U-shaped housing. The belt clip 14 used to secure the device 10 to a belt (not shown) or over the rim of a pair of trousers (not shown). The belt clip 14 is disposed on the back side of the device 10, as shown. The belt clip 14 can of course be modified as desired to provide virtually unlimited options for attaching the device 10 to an article of clothing or to some other object, for example to a ladder (not shown). The belt clip 14 is not shown in the other drawing figures for improved clarity of the elements that are shown.

There are many ways possible to construct the device 10 and many materials may be used. While the device 10 is capable of retaining a great variety of types and sizes of the glove 12, it is also possible to vary the size and construction of the device 10 to better accommodate any of these variations.

The U-shaped housing 16 is formed of steel, plastic, or other material, as desired. It includes a back wall 16a and two opposing side walls 16b, 16c. The back wall 16a and each of the two opposing side walls 16b, 16c are in perpendicular planar alignment. The two opposing side walls 16b, 16c are each attached on one edge thereof to the back wall 16a. The two opposing side walls 16b, 16c are in parallel planar alignment with each other and are disposed a predetermined distance apart from each other.

A door panel 18 is hingedly attached at one end thereof to the side wall 16c. The door panel 18 is attached to the side wall 16c at a wall end 17a of the side wall 16c and is disposed distally away from the back wall 16a. A spring 20 is used to supply a force that normally retains the door panel 18 in a closed position where a remaining end of the door panel 18 is disposed adjacent to a second wall end 17b of the remaining side wall 16b.

When the door panel 18 is closed, the door panel 18, back wall 16a, and the two side walls 16b, 16c form a substantially rectangular box shape with open ends at the top and the bottom. This is the position the device 10 normally occupies during use.

While the back wall 16a is shown as including a slight radius, it too can be a planar member, as desired.

Attached to one of the side walls 16c is a first arcuate planar member 22. A pair of fasteners 24 are used to secure the first arcuate planar member 22 to the side wall 16c. The fasteners 24 may include welding, rivets, or bolts and nuts, or even an adhesive may be used, as desired.

The first arcuate planar member 22 includes an upper planar area 24 that is adjacent to and in parallel planar alignment with the side wall 16c. An S-shaped arcuate portion 26 extends away from the side wall 16c and terminates at a lower planar area 28. The lower planar area 28 is disposed away from the side wall 16c and is in substantial parallel planar alignment with the side wall 16c.

The first arcuate planar member 22 includes a sufficient spring constant to allow it to flex repeatedly toward the side wall 16c and, as needed, to extend therefrom. This is described in greater detail hereinafter.

Disposed intermediate the first arcuate planar member 22 and the side wall 16c is a first foam spacer 30. The first foam spacer 30 is held in place by an adhesive or any method as may be desired. The first foam spacer 30 supplies additional force that resists compression and tends to urge the lower planar area 28 of the first arcuate planar member 22 away from the side wall 16c. A lesser spring constant is therefore required of the first arcuate planar member 22.

An additional benefit is also provided in that it is possible to vary the "feel" of the device 10 by varying the density of the first foam spacer 30. For lighter duty applications a lighter, more easily compressible material is used than for heavier duty applications. A lady who is gardening may not want to experience either a strong resistance in order to displace the first arcuate planar member 22 and compress the first foam spacer 30 nor have to overcome a substantial force to insert her hand (as is described hereinafter) generally into the device 10. Conversely, a welder wearing heavy thick gloves may not mind doing so.

A second arcuate planar member 32 is included on the remaining side wall 16b as is a second foam spacer 34. The second arcuate planar member 32 and the second foam spacer 34 are identical to these elements as previously described above and are attached in like manner to the remaining side wall 16b so that the lower planar area 28 of each are disposed proximate to each other.

Attached to each of the lower planar areas 28 are a plurality of downward facing bristles 36. The bristles 36 face each other and, because they face downward, allow easy insertion of the glove 12 that is worn over a hand 38 in a downward direction into the device 10. The downward facing bristles 36 do not substantially oppose motion in this direction.

As the gloved hand 38 is pushed downward into the device 10, the belt clip 14 retains the device 10 at the proper elevation. Accordingly, as the gloved hand 38 is pushed further downward, the bristles 36 fold flat against the lower planar areas 28 and the lower planar areas 28 and portions of each of the S-shaped arcuate portions 26 are urged in toward the respective side walls 16b, 16c an amount that is sufficient to accommodate the thickness of the gloved hand 38.

When the gloved hand 38 has been inserted sufficiently far down into the device, the downward motion of the hand 38 is stopped and the hand is withdrawn from the device in an opposite or upward direction. The bristles 36 "bite" into the glove 12 retaining the glove 12 in the device 10 as the hand is withdrawn from the device 10. The bristles 36 are selected of a firmness, type, and length that is well suited for the intended application and, as such, they do not penetrate through the glove 12 nor do they cause discomfort to the user.

Accordingly, the user merely pushes his hand 38 down into the device 10 and then withdraws his hand 38 back up again. This motion results in the glove 12 being automatically removed from the hand 38. Furthermore, the glove 12 is continually held in position in the device 10 by the force that is applied to the glove 12 by the arcuate planar members 22, 32 and by the foam spacers 30, 34.

To remove the glove 12, the user has two choices. He can reach under the device 10, grab a portion of the glove 12 that extends therefrom (i.e., the fingers), and continue to pull the glove 12 in a downward direction until it is removed from the device 10.

Alternatively, the user may pivot the door panel 18 into an opened position (as shown), grasp the glove 12 and pull it out sideways. It may help to also apply a downward force as well.

Accordingly, the device 10 provides for easy, effortless removal of the glove 12 from the hand 38 and for safe secure storage of the glove 12 until it is again needed. Furthermore, the glove 12 may be easily removed apart from the device 10 for use when needed.

A third option also exists when the glove 12 becomes contaminated and must be disposed of. The device 10 and all component parts thereof are formed of inexpensive flexible plastic and the device(s) 10 is/are discarded after use along with the contaminated glove(s).

Figure 3:
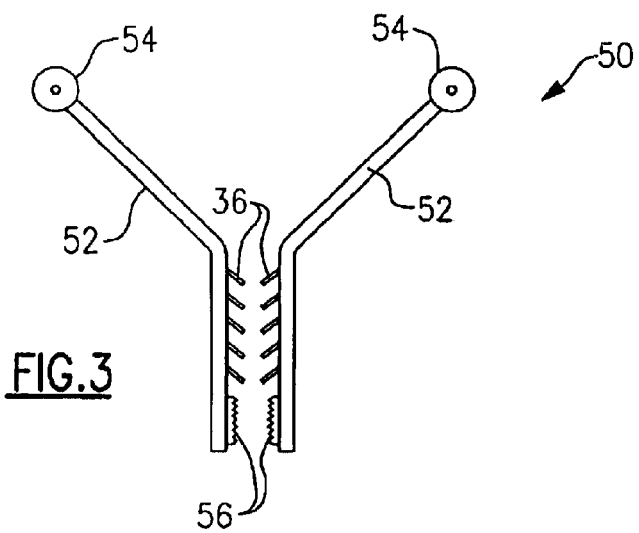
FIG. 3 is a cross sectional view of a portion of a modified glove retaining device.

Referring now to FIG. 3 is shown a portion of a modified glove retaining device 50 to illustrate some of the variations possible in constructing the modified device 50.

The housing 16 has been eliminated from this view. A pair of planar levers 52 are disposed on opposite sides of the housing 16 and are spring loaded to each pivot about an axis 54 so that the levers 52 are urged toward each other, as shown.

The bristles 36 are attached as desired to a lower portion of each of the levers 52 that are proximate each other. The modified device 50 is used in identical manner, only the bristles attached to the levers 52 are used to retain the glove 12 in position.

If desired, the bristles 36 can be eliminated and any type of a friction increasing abrasive 56 may be used for either the modified device 50 or with the device 10.

The modified device 50 is not as comfortable or effective to use as the device 10 because the levers 52 will tend to continue moving toward each other as the hand 38 is withdrawn from the modified device 50. This squeezes the hand 38 and is not comfortable. If desired, a limit stop (not shown) can be included to limit the amount of inward motion by the levers 52.

It is possible to insert a second glove (not shown) into the device 10 or modified device 50, however this is not preferred because the act of doing so may displace the first glove 12 downward and out of the device. If a second glove is to be inserted, the first glove 12 may need to be held by the opposite hand. Otherwise the procedure is as previously described. It is preferably to use two of the devices 10, one on each side of a torso (not shown) of the user. This allows the user to insert each hand downward instead of having to stretch across his abdomen and then downward.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A glove retaining device, comprising:
   (a) a portable housing;
   (b) means for receiving a hand when said hand is wearing said glove, said means for receiving a hand attached to said portable housing;
   (c) means for retaining said glove in said portable housing when said hand is withdrawn from said portable housing; and
   (d) means adapted for securing said glove retaining device to a belt, an article of clothing, or a ladder, said means for securing attached to said portable housing.

2. The glove retaining device of claim 1 wherein said means for receiving a hand is adapted to receive said hand when said hand is urged into said device in a first direction.

3. The glove retaining device of claim 2 wherein said first direction includes a downward direction.

4. The glove retaining device of claim 1 wherein said means for retaining said glove in said portable housing includes means for removing said glove from said hand when said hand is withdrawn from said portable housing in a second direction.

5. The glove retaining device of claim 4 wherein said second direction includes an upward direction.

6. The glove retaining device of claim 1 including means for removing said glove from said hand.

7. A glove retaining device, comprising:
   (a) a portable housing;
   (b) means for receiving a hand when said hand is wearing said glove, said means for receiving a hand attached to said portable housing and wherein said means for receiving a hand is adapted to receive said hand when said hand is urged into said device in a first direction;
   (c) means for retaining said glove in said portable housing when said hand is withdrawn from said portable housing and wherein said means for retaining said glove in said portable housing includes means for removing said glove from said hand when said hand is withdrawn from said portable housing in a second direction; and
   (d) means adapted for securing said glove retaining device to a belt, an article of clothing, or a ladder, said means for securing attached to said portable housing.

8. A glove retaining device, comprising:
   (a) a U-shaped housing having an open top and an open bottom, a back wall, and two opposing side walls, each of said two opposing side walls in parallel planar alignment and disposed a predetermined distance apart from each other;
   (b) a pair of arcuate members, one of said pair of arcuate members attached to an inside of each of said side walls, and wherein each of said pair of arcuate members includes a lower portion that is disposed away from each of said side walls and is in closer proximity to a remaining one of said pair of arcuate members than is a top portion thereof; and (c) a plurality of downward facing bristles disposed on each of said lower portions and wherein said plurality of bristles of one of said arcuate members faces said plurality of bristles on a remaining one of said arcuate members.

9. The glove retaining device of claim 8 including a foam spacer disposed intermediate said arcuate member and said side wall.

10. The glove retaining device of claim 8 including a door panel that is hingedly attached to one of said side walls, and wherein when said door panel is disposed in a closed position, said U-shaped housing devices a rectangular three dimensional structure having an open top end and an open opposite bottom end.

11. A method for removing a glove from a hand, comprising the steps of:

(a) providing a glove retaining device that is adapted to remove said glove from said hand and to retain said glove in said device and wherein said glove retaining device includes:

(1) a portable housing;

(2) means for receiving a hand when said hand is wearing said glove, said means for receiving a hand attached to said portable housing;

(3) means for retaining said glove in said portable housing when said hand is withdrawn from said portable housing; and (4) means adapted for securing said glove retaining device to a belt, an article of clothing, or a ladder, said means for securing attached to said portable housing;

(b) inserting said hand that includes said glove into said device in a first direction; and (c) removing said hand in an opposite second direction;

wherein said glove is retained in said device after said hand has been removed from said device.

* * * * *